(12) United States Patent
Mayer (10) Patent No.: US 11,896,345 B2
(45) Date of Patent: Feb. 13, 2024

(54) DEVICE FOR PRODUCING AN IMAGE OF DEPTH-DEPENDENT MORPHOLOGICAL STRUCTURES OF SKIN LESIONS

(71) Applicant: FOTOFINDER SYSTEMS GMBH, Bad Birnbach (DE)

(72) Inventor: Andreas Mayer, Bad Birnbach (DE)

(73) Assignee: FOTOFINDER SYSTEMS GMBH, Bad Birnbach (DE)

( * ) Notice: Subject to any disclaimer, the term of this patent is extended or adjusted under 35 U.S.C. 154(b) by 24 days.

(21) Appl. No.: 17/637,873

(22) PCT Filed: May 13, 2020

(86) PCT No.: PCT/DE2020/200035
§ 371 (c)(1),
(2) Date: Feb. 24, 2022

(87) PCT Pub. No.: WO2021/037315
PCT Pub. Date: Mar. 4, 2021

(65) Prior Publication Data
US 2022/0303506 A1 Sep. 22, 2022

(30) Foreign Application Priority Data
Aug. 26, 2019 (DE) ...................... 10 2019 122 843.3

(51) Int. Cl.
*H04N 7/18* (2006.01)
*A61B 5/00* (2006.01)
(Continued)

(52) U.S. Cl.
CPC .......... *A61B 5/0077* (2013.01); *A61B 5/0068* (2013.01); *A61B 5/444* (2013.01);
(Continued)

(58) Field of Classification Search
CPC ..... A61B 5/0077; A61B 5/0068; A61B 5/444; A61B 5/7425; G06V 10/454; G06V 10/02;
(Continued)

(56) References Cited

U.S. PATENT DOCUMENTS 6,479,729 B1 * 11/2002 Campochiaro .... A01K 67/0278
800/18
9,427,187 B2 * 8/2016 Gilbert ................. A61B 5/0059
(Continued)

FOREIGN PATENT DOCUMENTS

JP 2008023015 A * 2/2008

*Primary Examiner* — Jonathan R Messmore
(74) *Attorney, Agent, or Firm* — Dickinson Wright PLLC; Andrew D. Dorisio (57) ABSTRACT

A device for producing a plurality of images for assisting in characterizing skin lesions, the device includes a capturing unit for selectively illuminating and capturing recordings of an area of skin presenting a skin lesion, the capturing unit comprising magnifying optics providing at least 160× optical magnification of the area of skin for capturing morphological structures of the skin lesion; a focusing unit associated with the magnifying optics and configured to place a focal plane of the magnifying optics in a plurality of different depth planes below a skin surface of the area of skin starting from the skin surface; a control unit configured to control the focusing unit or the capturing unit and preferably controlling them in such a manner that the capturing unit captures a recording when the focal plane is located in a respective depth plane; and a processing and output unit for image production based on the image information provided by the capturing unit.

16 Claims, 2 Drawing Sheets

(51) Int. Cl.
| | |
|---|---|
| *G03B 13/36* | (2021.01) |
| *H04N 23/55* | (2023.01) |
| *H04N 23/56* | (2023.01) |
| *H04N 23/69* | (2023.01) |
| *H04N 23/80* | (2023.01) |
| *H04N 23/63* | (2023.01) |
| *H04N 23/959* | (2023.01) |
| *G06V 10/82* | (2022.01) |
| *G06V 10/44* | (2022.01) |

(52) U.S. Cl.
CPC ............ *A61B 5/7425* (2013.01); *G03B 13/36* (2013.01); *G06V 10/454* (2022.01); *G06V 10/82* (2022.01); *H04N 7/183* (2013.01); *H04N 23/55* (2023.01); *H04N 23/56* (2023.01); *H04N 23/635* (2023.01); *H04N 23/69* (2023.01); *H04N 23/80* (2023.01); *H04N 23/959* (2023.01)

(58) Field of Classification Search
CPC .... H04N 23/635; H04N 23/959; H04N 23/69; H04N 23/80; H04N 23/56; H04N 23/55; H04N 7/183
See application file for complete search history.

(56) References Cited

U.S. PATENT DOCUMENTS

| | | | |
|---|---|---|---|
| 2002/0010394 A1* | 1/2002 | Zavislan | ............... G16H 80/00 600/407 |
| 2008/0186591 A1 | 8/2008 | Altshuler et al. | |
| 2010/0302358 A1 | 12/2010 | Chen et al. | |
| 2018/0061046 A1 | 3/2018 | Bozorgtabar et al. | |

* cited by examiner

DEVICE FOR PRODUCING AN IMAGE OF DEPTH-DEPENDENT MORPHOLOGICAL STRUCTURES OF SKIN LESIONS

TECHNICAL FIELD

The invention relates to a device and a method for producing images for assisting in characterizing skin lesions of a human body.

BACKGROUND

A method known from the state of the art for capturing skin lesions, i.e., of skin changes and skin damage, is dermatoscopy or reflected-light microscopy, a non-invasive examining procedure in which the areas of skin to be examined are observed using a reflected-light microscope under illumination with polarized light at about 10× to 20× magnification in order to identify and assess the shapes and structures typical for certain benign and malignant types of lesions. The treating physician will render an assessment or a diagnosis by visual examination. The diagnosis can be confirmed by an additional histological examination of the area of skin, which requires a surgical procedure for removing a tissue sample, however. Since the advent of computer technology, individual digital images have also been produced and stored for this purpose in order to compare or evaluate them at a later time.

Likewise, it is known for a recording of the respective skin lesion to be produced using a known video dermatoscope, for example, and to display it in the form of individual images in appropriate output means for evaluation by the respective treating physician and to store it digitally for later comparison or analysis.

SUMMARY

The object of the present invention is to further improve the known devices and methods. In particular, an optimized imaging device for capturing and characterizing a skin lesion which enables the treating physician to better identify malignant and benign skin tissue is to be provided. This object is attained by the subject matter of the dependent claims. The dependent claims constitute advantageous embodiments of the present invention. Moreover, the invention addresses other issues, which will be discussed in more detail in the following description.

In a first aspect, the invention relates to a device for producing a plurality of images for assisting in characterizing skin lesions, the device comprising a capturing unit, in particular a video dermatoscope, for selectively illuminating and capturing recordings of an area of skin presenting a skin lesion, the capturing unit comprising magnifying optics providing at least 160×, preferably at least 240×, optical magnification of the area of skin for capturing individual morphological structures of the skin lesion; a focusing unit associated with the magnifying optics and configured to place a focal plane of the magnifying optics in a plurality of different depth planes below a skin surface of the area of skin starting from the skin surface, preferably in steps; a control unit configured to control the focusing unit and/or the capturing unit and preferably controlling them in such a manner that the capturing unit captures a recording, preferably in the form of a video or an individual image, when the focal plane is located in a respective depth plane; and a processing and output unit for image production based on the image information provided by the capturing unit.

Unlike conventional dermatoscopy, the present invention makes it possible to optically capture and subsequently produce an image of or visualize morphological structures, in particular capillaries and cellular structures in different depth planes of a skin lesion to be examined with the aid of the highly magnifying optics, the associated focusing unit, and a capturing unit connected thereto, preferably in the form of a video or digital camera, in particular a video dermatoscope. The images produced in this manner are comparable to slice images as they are produced in histology using a microscope. Contrary to this, however, the device according to the invention makes it possible to directly obtain color images of the morphological structures without having to take tissue samples and examine them using a slide under an optical microscope. Moreover, the present invention makes it possible to provide color images of the morphological structures without dyeing techniques, which are typically used in a histological examination. The detail images provided as video and/or individual images enable a treating physician to analyze the morphological structures of skin lesions in detail. In particular, this involves making morphological (cellular) structures visible or displaying them in different depth planes of a skin lesion, which can be immediately evaluated by the treating physician and offer additional diagnostic options of a lesion compared to conventional dermatoscopy.

The magnifying optics of the capturing unit preferably allows at least 160× to 400×, more preferably at least 240× to 400× and further preferably at least 300× to 400×, optical magnification of the area of skin to be examined or a lesion to be examined in the area of skin. The magnifying optics and the associated focusing unit can be integrated in a preferably exchangeable front-end module for a camera module of the capturing unit. The capturing unit is preferably configured as a mobile or portable handheld device.

The focusing unit can comprise manual and/or automatic adjusting means which selectively vary a respective focal plane of the magnifying optics. The focusing unit is preferably configured to vary a distance between lenses of the magnifying optics and/or a distance between a group of lenses and the camera module of the capturing unit. The adjusting means can comprise an electric motor and/or a micro-actuator, for example. Manual or automatic adjustment can take place, for example, with the aid of a manually operable control element, such as a turning ring or a rotary and/or control knob, with the aid of the control unit of the device, and/or with the aid of the processing and output unit. A user can adjust the intended focal plane below the skin surface in the µm range.

The focusing unit is preferably configured to preferably automatically focus a surface of the area of skin to be examined or of a lesion in the course of an initialization, such as during or shortly after being positioned on the lesion, in particular when the capturing unit is placed on the area of skin presenting the lesion.

The focusing unit is preferably configured to not only focus the magnifying optics on a skin surface or a lesion surface but also to selectively place the focal plane in a depth plane of 1 µm to 50 µm, more preferably 5 µm to 50 µm, below the skin surface. In other words, a depth plane which is located 1 µm to 50 µm, more preferably 5 µm to 50 µm, below a preferably initially focused skin surface is preferably selectively focused in the process. Thus, detailed (cell) structure recordings can be captured to a depth of up to 50 µm below the skin surface and be displayed by the processing and output unit. Depth-dependent recordings or images of the morphological structures of the lesion can be captured and displayed for analysis by the treating physician.

The focusing unit is preferably configured to automatically or manually vary the focal plane in steps of 1 μm to 7 μm, preferably in steps of 2.5 μm to 5 μm, in particular below the skin surface.

The control unit is preferably configured to control the focusing unit and/or the capturing unit in such a manner that an image or a recording is captured in a respective depth plane and/or the respective image is stored.

The control unit is preferably configured to control the focusing unit and/or the capturing unit in such a manner that a predefined number of depth planes and/or predefined discrete depth planes are focused selectively and/or in one sequence—preferably after an initialization or a focusing on the skin surface—and a corresponding capturing by the capturing unit takes place. In this context, a sequence refers to a consecutive control, preferably in a time frame of 1 to 30 seconds, more preferably in a time frame of 1 to 15 seconds. The predefined depth planes preferably comprise at least 2 to 20, more preferably at least 5 to 15, predefined depth planes, which are preferably focused one after the other in steps for image capturing. For example, a control to the depth planes at 5 μm, 20 μm, 25 μm, 30 μm below the skin surface can take place within one predefined sequence, an image or recording being captured after focusing each of these depth planes. The control unit and/or the processing and output unit can be configured to create, vary, and store predefined sequences.

The capturing unit preferably has illuminating means integrated therein or connectable thereto, preferably a plurality of LED light sources or LED chips emitting white light in particular. The illuminating means are preferably configured to illuminate the skin surface to be examined with polarized light, in particular linearly polarized and/or cross-polarized light. The LED light sources preferably have a color temperature of 5400 K to 5600 K. The color rendering index Ra of the LED light sources is preferably at least 92, more preferably at least 95 and further preferably at least 97. The illuminating means are preferably configured to illuminate the skin surface or the lesion by reflected-light illumination, in which the light source is disposed at a predefined distance to the skin surface, and/or to couple light directly into the skin, in which case the illumination is provided by a light source disposed directly on the skin surface. An immersion gel can be applied to the skin surface to be examined, on which the capturing unit or a front-end module of the capturing unit is then placed, in order to reduce the refraction of light on the skin surface.

The device can comprise a positioning unit which is configured to selectively project a marking, in particular a dot or cross-line laser, onto the area of skin or onto the lesion located therein. The positioning unit can be disposed directly on the capturing unit or be configured separately therefrom. Once the magnifying optics has been positioned on the area of skin to be examined, the positioning unit can be switched off.

The device preferably comprises an RGB sensor for capturing the respective image information and producing an image based thereon. The RGB sensor is preferably comprised by a camera module of the capturing unit. The image information provided by the RGB sensor are used by the processing and output unit to produce images, in particular color images, of the respective depth plane.

The device can comprise other sensors in addition to an RGB sensor, such as an IR sensor, a multi-spectral sensor for detecting electromagnetic radiation in at least 4 to 12 predefined wavelength ranges, or a hyperspectral sensor for detecting electromagnetic radiation in at least 8 to 20 predefined wavelength ranges. In this case, the processing and output unit is preferably configured to produce one or multiple images based on the RGB, IR and/or multi-spectral or hyperspectral image information. Additional illuminating means, in particular additional infrared or UV (LED) light sources, can be provided for capturing the multi-spectral or hyperspectral image information.

The processing and output unit of the device can be configured as a computing unit, in particular as a personal computer (PC) or a mobile device, in particular as a laptop, a tablet or a smartphone, with associated control software. The control unit can be part of the computing unit. The computing unit is connected to the capturing unit via cable or wirelessly.

The processing and output unit preferably comprises at least one memory unit and a display for displaying the captured or produced images. For the displaying according to the invention, the processing and output unit preferably has a graphical interface of a software program for controlling the device. Moreover, the processing and output unit preferably comprises a user interface, such as a keyboard, a mouse and/or a touch display, for controlling the processing and output unit, the control unit or an associated software program. The processing and output unit can additionally be connected to at least one external server.

Moreover, the device can comprise another capturing unit, in particular in the form of a digital photo camera, and/or another exchangeable front-end module for the capturing unit, which is configured to capture a clinical overview image (overview image) of the patient or a reference overview image (reference image) of a skin lesion to be examined. The latter has a significantly lower optical magnification than the magnifying optics according to the invention. The term overview image refers to a total or partial body recording of a patient, in which at least one or a plurality of skin lesions to be examined are depicted. The term reference image of the skin lesion to be examined refers to an individual recording of a skin lesion, which shows the skin lesion at preferably 10× to 25×, more preferably 15× to 20×, optical magnification.

In a preferred embodiment, the processing and output unit is configured to display a respective detail image of the captured morphological structures of the skin lesion, in particular a cell structure image, in a respective depth plane below the skin surface as a focused live video image and/or as an individual image. The detail image is preferably displayed in combination with a variable control element for displaying and/or adapting the respective depth plane. A user can thus use the control element to preferably directly focus or select the respective depth plane. Furthermore, a user can take and store snapshots of a live video image.

The processing and output unit can be configured to provide a live video image mode in particular for the purpose of positioning the capturing unit. The focused surface of the area of skin or of the lesion and the captured image information are displayed as a live video image, i.e., output in a display of the processing and output unit. The user can scan or trace the surface of the area of skin and position the capturing unit at the desired position for detailed analysis. Once the capturing unit is directed at the desired position, manual switching to an individual image or frame mode can take place. Alternatively, the processing and output unit can be configured to detect a stationary or unchanging direction of the capturing unit after an initial positioning and can automatically switch to an individual image or frame mode. Therein, the individual images can be captured in the respective depth planes.

Alternatively, a live video image of the captured image information can be output in the respective focused depth plane as described above. When the position changes in the live video image mode, snapshots taken by the user within a depth plane can be stored, which then at least partially overlap and which can be joined in a coherent individual image by the processing and output unit using a known stitching algorithm.

The processing and output unit is preferably configured to display a the detail image of morphological structures of the skin lesion, either as a live video image or as an individual image rendering, which are captured in a respective depth plane, in combination with a captured reference image of the skin lesion. The reference image depicts the skin lesion preferably in its entirety; i.e., the respective outer contours of the individual skin lesion are visible in the image. The combined depiction enables a user to simultaneously analyze the respective detail image and the associated reference image of the lesion.

The processing and output unit is preferably configured to display an indicator for the respective current position of the displayed detail image of the skin lesion in the reference image. The indicator can be a border, such as a polygonal, in particular rectangular, marking of the current position of the capturing unit in the reference image. When the respective position of the capturing unit changes, this is preferably indicated or displayed by the indicator. The respective capturing and displaying of the position in the reference image can take place by means of a software algorithm of the processing and output unit, which uses image evaluation to track both an initial positioning of the capturing unit on the skin lesion and a corresponding movement of the capturing unit relative to the skin lesion during the examination and calculates it for a rendition in the reference image. For the respective capturing, additional positioning means for detecting a current position of the capturing unit on a surface of the area of skin or of the lesion can also be provided, which are connected to the processing and output unit.

Furthermore, the processing and output unit is preferably configured to display a (clinical) overview image of a patient in combination with the respective detail image of the skin lesion and/or with a captured reference image of the skin lesion. The overview image preferably contains an indicator for the respective position of the depicted skin lesion in the clinical overview image. The indicator can be a border, such as a polygonal, in particular rectangular, marking of the current position of the lesion in the overview image.

The processing and output unit preferably comprises a processor and memory unit (computing means), which preferably comprises a corresponding software algorithm, the processor and memory unit being configured to pre-characterize and/or assess the respective captured detail image of morphological structures of the skin lesion, preferably using artificial intelligence, and to output an associated information based thereon, preferably in the form of a risk value, and/or an identified skin lesion class, using the processing and output unit. The computing means are preferably configured to analyze the captured detail images of morphological structures of the respective depth planes using artificial intelligence, in particular by means of an artificial neural network trained for this purpose. The latter can in particular be trained to distinguish morphological structures of non-melanocytic and melanocytic skin lesions. The artificial neural network can additionally be trained to identify morphological structures of a plurality of the following types of skin lesions as classes: melanocytic nevus, dermatofibroma, malignant melanoma, actinic keratosis and Bowen's disease, basal-cell carcinoma, seborrheic keratosis, liver spots, angioma, and/or squamous-cell carcinoma.

In a preferred embodiment, the artificial neural network is configured to identify predefined risk classes, in particular regarding a malignity of the skin lesion. A respective risk class can reflect a respective degree of advancement of a skin lesion. For example, the artificial neural network can be configured to identify at least two, preferably at least three, different degrees of advancement and therefore risk classes of a respective skin lesion which are associated with them by analyzing the respective morphological structures. For example, they can be categorized as belonging to a low, an intermediate or a high risk class. A higher risk class can comprise degrees of advancement of skin lesions which are to be considered as being of higher risk to the human and which require timely treatment and/or surgical intervention. Further preferably, the artificial neural network is configured to distinguish between a plurality of different degrees of advancement of a type of skin lesion. The respective association with corresponding risk classes can be performed by the artificial neural network itself and/or by a calculation following the processing by the artificial neural network.

In a preferred embodiment, a preferably numerical risk value of the respective skin lesion is output and/or calculated based on a respective identified or calculated risk class of types of skin lesions and/or based on a respective identified degree of advancement of the skin lesion. The numerical value is preferably between 0.1 and 1. A value between 0.1 and 0.2 can be defined as a low value, a value between 0.2 and 0.49 can be defined as an intermediate value, and a value between 0.5 and 1.0 can be defined as a high risk value.

The processing and output unit is preferably configured to display the pre-characterization and/or the assessment of the respective captured detail image, in particular in combination with the respective reference image of the skin lesion. An output of the pre-characterization and/or the assessment, such as the display of a risk class and/or a risk value and/or an identified skin lesion class, preferably takes place in real time or without any substantial delay, i.e., within 1 to 20 seconds, more preferably within 1 to 10 seconds.

The artificial neural network can be a known convolutional neural network (CNN). The artificial neural network preferably has at least one hidden layer, more preferably between 1 and 100, most preferably between 1 and 20 hidden layers. In a preferred embodiment, the artificial neural network has between 2 and 10,000, preferably between 2 and 1000 neurons per layer.

The artificial neural network is preferably configured to identify a predefined classification based on knowledge taught by monitored learning. A large number of morphological structures of skin lesions of various types, different nature, and/or different progression according to a respective diagnosis are provided to the artificial neural network, preferably as image data, for training in a known manner by trained learning. They can in particular be provided from histological examinations. A training of this kind can be reviewed in a known manner in a subsequent validation process with regard to the precision of identification of the trained artificial neural network. Moreover, an artificial neural network already trained with a large dataset can be used and be adapted to the respective type of use with little parameter changes by means of known transfer learning. The training and validation of the artificial neural network can take place using Python TensorFlow and/or Python Keras, for example. The image processing, the provision and/or the association can take place using OpenCV2.4.

The artificial neural network can additionally be configured to further improve previously learned knowledge in the ongoing analysis of the skin lesions from the supplied image data of the morphological structures. This means that the artificial neural network is preferably self-learning and continuously adds to or improves its knowledge during the ongoing use in analyzing images of the morphological structures. For example, information provided by the treating physician regarding a respective diagnosis of a captured skin lesion can be taken into account.

In another aspect, the invention relates to a method for producing a plurality of images for assisting in the characterization of skin lesions, preferably using a device as described above, the method comprising the following steps:

- illuminating an area of skin to be examined by means of illuminating means, preferably a plurality of LED chips;
- selectively focusing an optical capturing unit with associated magnifying optics on a plurality of different depth planes below a skin surface starting from the skin surface, preferably in steps, the magnifying optics allowing at least 160×, preferably at least 240×, optical magnification of the area of skin for capturing morphological structures of a skin lesion in the area of skin;
- capturing and preferably storing at least one recording of the skin lesion in a respective depth plane by means of a capturing unit;
- producing at least one detail image of morphological structures of the skin lesion based on the image information provided by the capturing unit.

The focusing into the respective depth planes preferably takes place automatically and in steps at predefined intervals. The latter can preferably be steps of 1 µm to 7 µm each, more preferably steps of 2.5 µm to 5 µm each. In a preferred embodiment, predefined depth planes are focused one after the other in one sequence, and at least one image is captured and stored or retained after each focusing. A respective detail image is preferably produced and/or output by a processing and output unit as a live image in real time, in particular in a first initialization, in the course of which the capturing unit is directed at the respective desired position of the skin lesion.

During the examination of the skin lesion, a larger area can be analyzed by changing the position of the capturing unit within a respective depth plane. This results in a plurality of individual images which overlap more or less and which can be used to calculate a coherent image in the respective depth plane by means of a known stitching algorithm. This coherent image can be output on a display for analysis by a treating physician.

Moreover, the method can comprise the further steps of capturing a skin lesion to be examined, preferably at 10× to 20× optical magnification, and displaying a reference image of the skin lesion in combination with an associated detail image of the skin lesion, preferably next to each other, on a display of a processing and output unit. In another step, an indicator can be additionally displayed, preferably in the reference image, said indicator marking a current position of the displayed detail image in the skin lesion.

Moreover, the method can comprise other features which have been described in connection with the device described above. Reference is made to the above description of the device in order to avoid redundancies. In particular, the features described above shall also be considered disclosed and claimable for the method according to the invention and vice-versa.

BRIEF DESCRIPTION OF THE DRAWINGS

Other advantages, features and details of the invention are apparent from the following description of preferred examples of configurations and from the drawings.

DETAILED DESCRIPTION

Figure 1:
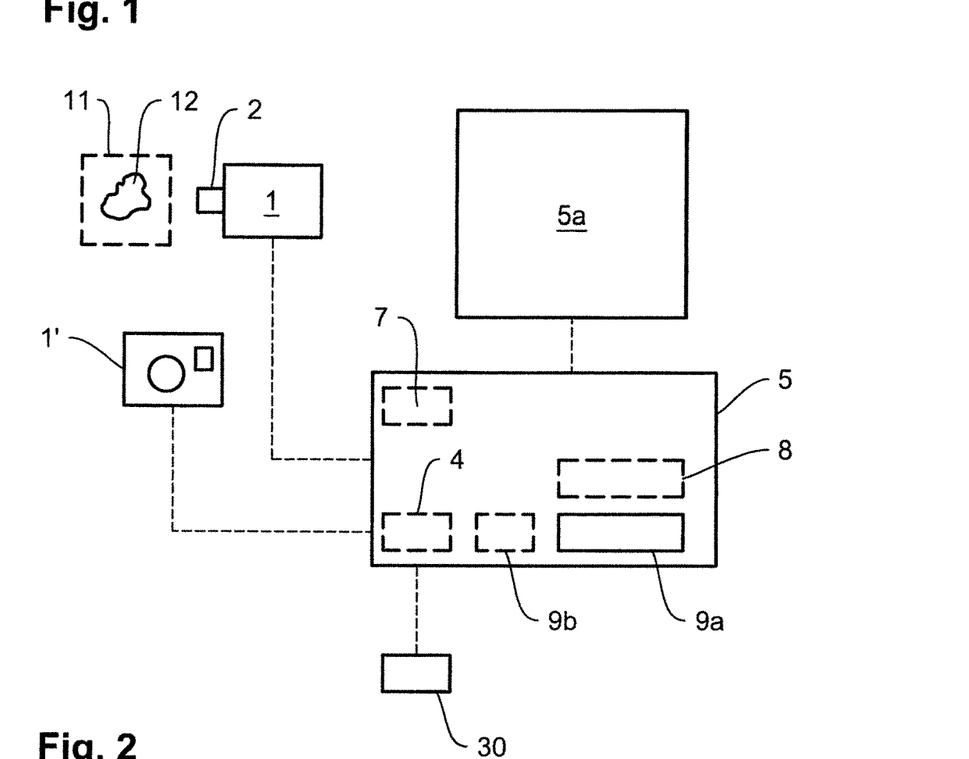
FIG. 1 is a schematic illustration of a preferred embodiment of the device according to the invention.

FIG. 1 shows a preferred embodiment of device 10 according to the invention. Device 10 comprises a capturing unit 1, which is configured to capture a recording or an image, in particular an optically highly magnified detail recording of morphological structures 13a of a skin lesion 12 in an area of skin 11 of a patient P (see FIG. 4). Capturing unit 1 preferably provides digital image information or a signal representing the latter based on the captured recording. Capturing unit 1 preferably comprises a known video dermatoscope. Capturing unit 1 can preferably be selectively operated in a video mode or an individual image mode. Capturing unit 1 has a magnification option 2 and a focusing unit 3 associated with the latter and is preferably configured as a mobile handheld device.

Device 10 can optionally comprise an additional capturing unit 1'. The latter can preferably comprise a high-resolution digital image or video camera and is configured to capture a reference image 14 of skin lesion 12 and/or a clinical overview image 16 of patient P.

Device 10 comprises a processing and output unit 5, which is connected to capturing unit 1, 1'. Processing and output unit 5 is configured to electronically process the provided image information or image data and to output corresponding images. For this purpose, processing and output unit 5 comprises at least one output unit in the form of a display 5a. The output unit can additionally be configured to provide acoustic signals or warning messages.

A control unit 4 of device 10 for controlling focusing unit 3 and/or capturing unit 1 can be integrated in processing and output unit 5 or be provided separately. Moreover, processing and output unit 5 comprises a processor and memory unit 8. The latter is preferably configured to store and execute a software program for controlling the device. Processing and output unit 5 preferably has a user interface 9a for controlling device 10 and/or a software executed thereon. User interface 9a can comprise known input means, such as a keyboard, a mouse, and/or a touchscreen.

In a preferred embodiment, processor and memory unit 8 of processing and output unit 5 comprises an artificial neural network, which is preferably stored thereon and configured to identify and/or classify morphological structures of skin lesions. The artificial neural network can access data stored in memory unit 8 and/or can access an external server or an external memory unit 30. The latter can be connected to processor and memory unit 8 via a communication interface 9b of processing and output unit 5. Communication interface 9b can additionally be configured to connect capturing unit 1, 1' to processing and output unit 5. Communication interface 9b can enable wireless and/or cable communication with capturing unit 1, 1' and/or the external server or an external memory unit 30.

Moreover, device 10 can comprise a positioning unit 7, which is configured to selectively project a marking, in particular a dot or cross-line laser, onto area of skin 11.

Figure 2:
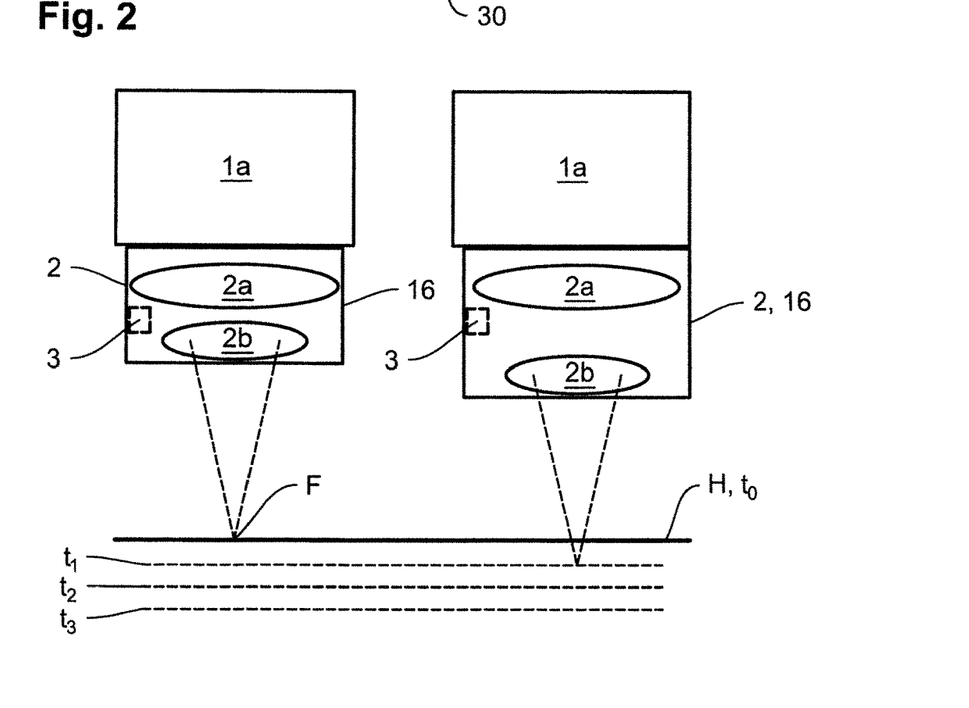
FIG. 2 is a schematic illustration of the magnifying optics and the associated focusing unit.

FIG. 2 shows a schematic illustration of magnifying optics 2 and associated focusing unit 3. Magnifying optics 2 is configured as a front-end module 1b for a camera module 1a of capturing unit 1 and can preferably be selectively connected to camera module 1a. Magnifying optics 2 is configured to provide at least 160×, more preferably at least 240×, optical magnification of area of skin 11 or of skin lesion 12 so that morphological structures 13a (see FIG. 4) can be captured in different depth planes of skin lesion 12. The magnifying optics preferably comprises at least two lenses 2a, 2b, which are adjustable relative to each other, and/or a lens module adjustable relative to camera module 1a.

Focusing unit 3 associated with magnifying optics 2 is preferably configured to vary a distance between lenses 2a, 2b of optics 2 and/or a distance between a lens module and camera module 1a of capturing unit 1. To this end, focusing unit 3 preferably comprises adjusting means in the form of an electric motor and/or a micro-actuator. The adjusting means can be controlled manually by an operator and/or automatically, in particular by means of associated control unit 4 and/or associated processing and output unit 5. As shown in FIG. 2, focusing unit 3 is configured not only to focus skin surface H of a skin lesion 12 to be examined, skin surface H corresponding to a zero depth plane $t_0$, but also to selectively focus a plurality of different depth planes $t_1, \ldots, t_n$ below skin surface H.

Focusing unit 3 is preferably configured to preferably automatically focus skin surface H as a first step in the course of an initialization once capturing unit 1 has been positioned on skin lesion 12. Focal plane F of magnifying optics 2 is placed in corresponding zero depth plane $t_0$ (see illustration on the left in FIG. 2). Subsequently, focal plane F can be adjusted to depth planes $t_1, \ldots, t_n$ located below skin surface H manually by a user and/or automatically by control unit 4 and/or by processing and output unit 5. In the illustration on the right in FIG. 2, for example, focal plane F is placed in a first depth plane $t_1$ below skin surface H, i.e., said first depth plane $t_1$ is focused.

Predefined depth planes $t_1, \ldots, t_n$ can be selectively focused individually or one after the other in steps in a predefined sequence, wherein respective recordings or images can be captured by capturing unit 1 in each of depth planes $t_1, \ldots, t_n$.

Focusing unit 3 is preferably configured to selectively place focal plane F in a depth plane of 1 μm to 50 μm, more preferably 5 μm to 50 μm, below the skin surface. Respective focal plane F can be automatically or manually varied in steps of 1 μm to 7 μm, more preferably in 2.5 μm to 5 μm.

Figure 3:
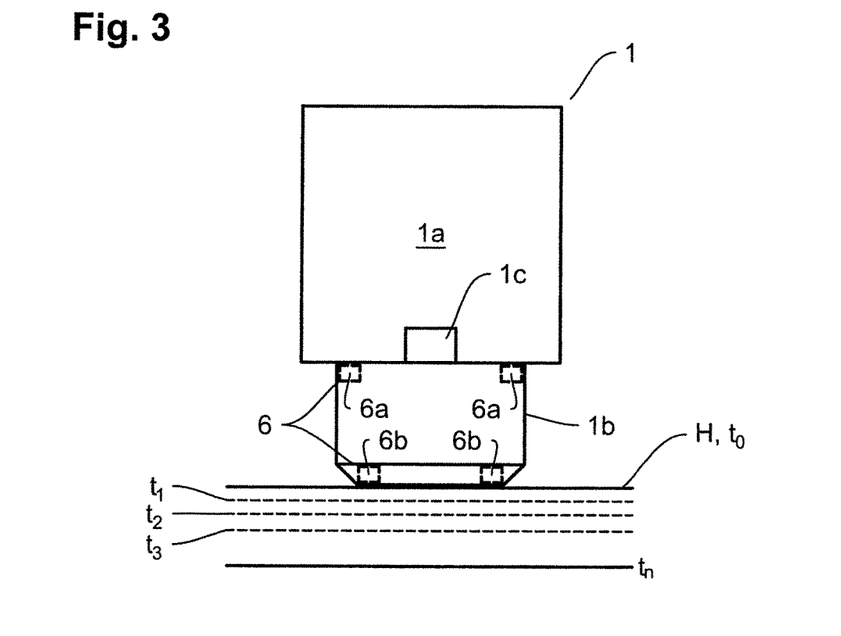
FIG. 3 is a schematic side view of a preferred embodiment of the capturing unit as a camera module with an exchangeable front-end module.

FIG. 3 shows a schematic side view of a preferred embodiment of capturing unit 1, which comprises camera module 1a with an exchangeable front-end module 1b. Capturing unit 1 preferably comprises illuminating means 6, preferably a plurality LED light sources or LED chips in particular emitting white light, which are integrated in or connectable to capturing unit 1. Illuminating means 6 preferably comprise illuminating means 6b disposed at the end of, i.e., distally on, capturing unit 1 for coupling light directly into the area of skin 11 to be examined. They are preferably in direct contact with skin surface H during the examination of area of skin 11. In order to reduce the refraction of light at the skin surface, an immersion gel can be applied, on which capturing unit 1 is then placed. Optionally, capturing unit 1 additionally comprises reflected-light illumination means 6a, which are disposed at a predefined distance to skin surface H. Furthermore, camera module 1a comprises a sensor system 1c for capturing the recordings or image information during the examination of illuminated lesion 12. Sensor system 1c preferably comprises at least one RGB sensor. Optionally, the sensor system can comprise other sensors for capturing image information during the examination of skin lesion 12 in the different depth planes $t_1, \ldots, t_n$, in particular an IR sensor, a multi-spectral sensor or a hyperspectral sensor.

Figure 4:
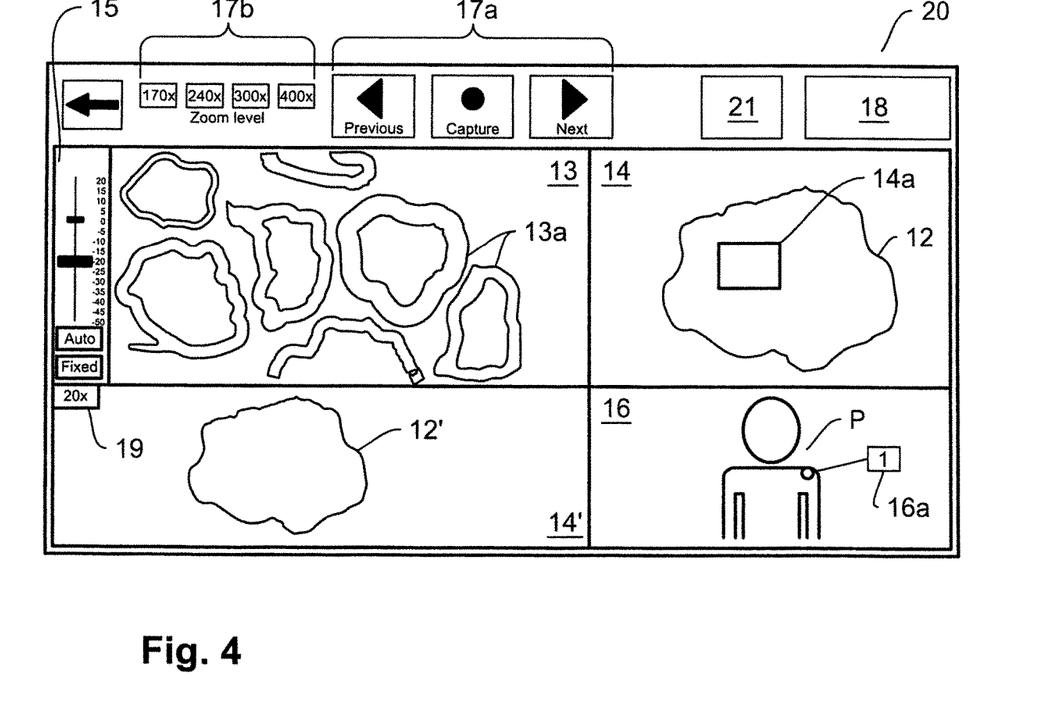
FIG. 4 is a preferred depiction of a situation in which the image of a skin lesion is output according to the invention with associated information.

FIG. 4 shows a preferred illustration of a situation in which the image of a skin lesion 12 is output according to the invention together with associated information by means of a display 5a of processing and output unit 5. The latter constitutes a graphical interface 20 on which at least one detail image 13 of morphological structures 13a, in particular cellular structures and/or capillaries, in a predefined depth plane of skin lesion 12 are displayed for analysis by a treating physician. Detail image 13 can be displayed as a live video image or as an individual image.

Graphical interface 20 is preferably provided by a control software of processing and output unit 5. Graphical interface 20 preferably comprises patient information 18, such as a name and an age of the person to be examined. Moreover, graphical interface 20 comprises control elements 17, in particular elements for display or recording control 17a and for selectively controlling a magnification by magnifying optics 17b.

In addition to detail image 13, graphical interface 20 preferably comprises a field 21 for displaying a pre-characterization and/or an assessment of currently captured lesion 12. In particular, a risk class, a preferably numerical risk value, and/or an identified skin lesions class can be displayed. They can be calculated or determined based on the evaluation of the captured recordings by means of artificial intelligence as described above.

Graphical interface 20 preferably comprises a control element 15, which is associated with detail image 13 and serves to display and/or adapt respective depth plane $t_1, \ldots, t_n$. In the latter case, a user can change the focused depth plane of capturing unit 1 selectively and preferably in predefined steps by shifting respective control element 15. Control element 15 has a scale with predefined steps for changing the focus in the unit "μm", preferably from +20 μm to −50 μm. Moreover, control element 15 can comprise an adjusting function for automatic ("auto") or manual ("fixed") focusing.

Furthermore, graphical interface 20 comprises a reference image 14 of skin lesion 12, which has a significantly lower optical magnification and in which skin lesion 12 is depicted completely. Reference image 14 preferably contains an indicator 14a, which shows the current position of detail image 13 in depicted skin lesion 12. A change in position of capturing unit 1 on skin lesion 12 is preferably displayed in reference image 14 in real time.

Moreover, graphical interface 20 can comprise another display of a reference image 14'. The latter can correspond to reference image 14 mentioned above but be displayed in such a manner that it can be changed by the user in terms of color rendition and/or size, for example. For this purpose, other reference image 14' can comprise associated image information 19, such as a magnification value.

Additionally, graphical interface 20 preferably comprises a clinical overview image 16 of patient P. The overview image preferably contains an indicator 16a, which shows the respective position of displayed skin lesion 12.

REFERENCE SIGNS 1 capturing unit
1a camera module
1b front-end module
1c camera sensor system
2 magnifying optics
3 focusing unit
4 control unit
processing and output unit
5a display
6 illuminating means
6a reflected-light illumination means
6b means for directly coupling in light
7 positioning unit
8 processor and memory unit (computing means)
9a user interface
9b communication interface
10 device
11 area of skin
12 lesion
13 detail image of morphological structures
13a morphological structures (cellular structures, capillaries)
14 reference overview image (overview image)
14a detail image position determination indicator
15 depth plane control element
16 clinical overview image
16a lesion position determination indicator
17 navigation and/or control elements
17a display/recording controller
17b magnification controller
18 patient information
19 image information
20 graphical interface
21 output of risk value and/or identified skin lesion class
30 external server
$t_1, \ldots, t_n$ depth planes
$t_0$ zero depth plane (skin surface)
F focal plane
H skin surface
P patient

The invention claimed is:

1. A device (10) for producing a plurality of images for assisting in characterizing skin lesions, the device comprising:
a capturing unit (1) configured to selectively illuminate and capture recordings of an area of skin (11) presenting a skin lesion (12), the capturing unit (1) comprising a camera and magnifying optics (2) providing at least 160× optical magnification of the area of skin (11) for capturing morphological structures of the skin lesion (12);
a focusing unit (3) comprising manual or automatic adjusting means associated with the magnifying optics (2) and configured to place a focal plane (F) of the magnifying optics (2) in a plurality of different depth planes (t1, . . . , tn) below a skin surface (t0) of the area of skin (11) starting from the skin surface;
a computing unit (4) comprising at least one processor and at least one memory, the computing unit configured to control the focusing unit (3) or the capturing unit (1) in such a manner that the capturing unit (1) captures a recording when the focal plane (F) is located in a respective depth plane (t1, . . . , tn), and the computing unit is configured for image production based on the image information provided by the capturing unit (1), wherein the computing unit (4) is configured to display a respective detail image (13) of morphological structures of the skin lesion (12) in a respective depth plane ($t_1, \ldots, t_n$) as a live video image and as an individual image in combination with a variable control element (15) for displaying and adapting the respective depth plane ($t_1, \ldots, t_n$) and in combination with a captured reference image (14) of the skin lesion (12).

2. The device according to claim 1, wherein the magnifying optics (2) allows 250× to 400× optical magnification of the area of skin (11).

3. The device according to claim 1, wherein the focusing unit (3) is configured to automatically or manually place the focal plane (F) in a depth plane (t1, . . . , tn) of 1 to 50 μm below the skin surface (t0).

4. The device according to claim 1, wherein the focusing unit (3) is configured to automatically or manually vary the focal plane (F) in steps of 1 to 7 μm.

5. The device according to claim 1, wherein the computing unit (4) is configured to control the focusing unit (3) or the capturing unit (1) in such a manner that a plurality of predefined depth planes (t1, . . . , tn) are focused one after the other in one sequence and at least one recording is captured in each depth plane.

6. The device according to claim 1, wherein the magnifying optics (2) and the associated focusing unit (3) are integrated in an exchangeable front-end module (1b) for a camera module (1a) of the capturing unit (1).

7. The device according to claim 1, wherein the capturing unit (1) comprises illuminating means (6) for reflected-light illumination (6a) or direct coupling in of light (6b) into the area of skin (2), the illuminating means (6) being integrated in or connectable to the capturing unit (1).

8. The device according to claim 1, wherein the device (10) comprises a positioning unit (7) configured to selectively project a marking onto the area of skin.

9. The device according to claim 1, wherein the computing unit (5) is configured to display an indicator (14a) for the respective current position of the displayed detail image (13) of the skin lesion (12) in the reference image (14).

10. The device according to claim 1,
wherein the computing unit (5) is configured to display a clinical overview image (16) of a patient (P) in combination with the respective detail image (13) of the skin lesion (12) or a captured reference image (14) of the skin lesion (12), the clinical overview image (16) containing an indicator (16a) for the respective position of the displayed skin lesion (12) in the clinical overview image (16).

11. The device according to claim 1, further comprising a processor and memory unit (8) configured to pre-characterize or assess the captured detail image (13) of morphological structures of the area of skin, and to output an associated information based thereon, by means of the processing and output unit (5).

12. A method for producing a plurality of images for assisting in characterizing skin lesions, using the device (10) according to claim 1, the method comprising the following steps:

- illuminating an area of skin (11) to be examined by means of illuminating means (6);
- selectively focusing an optical capturing unit (1) with associated magnifying optics (2) on a plurality of different depth planes (t1, ..., tn) below a skin surface (H) stating from the skin surface (H), the magnifying optics (2) allowing at least 160× optical magnification of the area of skin (11) for capturing morphological structures of a skin lesion (12) in the area of skin (11);
- capturing at least one recording of the skin lesion (12) in a respective depth plane (t1, ..., tn) by means of a capturing unit (1);
- producing at least one detail image (13) of morphological structures of the skin lesion (12) based on the image information provided by the capturing unit (1);
- displaying, with a computing unit, a respective detail image (13) of morphological structures of the skin lesion (12) in a respective depth plane ($t_1$, ..., $t_n$) as a live video image and as an individual image; and
- displaying and adapting, with a variable control element (15), the respective depth plane ($t_1$, ..., $t_n$) and in combination with a captured reference image (14) of the skin lesion (12).

13. The method according to claim 12, wherein the focusing into the respective depth planes takes place automatically and in steps at predefined intervals.

14. The method according to claim 12, wherein predefined depth planes (t1, ..., tn) are focused one after the other in one sequence and at least one recording is captured and stored after the respective focusing.

15. The method according to claim 12, the method comprising the following further steps:

- capturing a skin lesion (12) to be examined; and displaying the reference image (14) of the skin lesion (12) in combination with the associated detail image (13) of the skin lesion (12) on a display (5a) of the computing unit (4).

16. The method according to claim 15, the method comprising the further step of displaying an indicator (14a) for marking a current position of the displayed detail image (13) in the skin lesion (12).

* * * * *